United States Patent [19]

Porter et al.

[11] 4,257,776

[45] Mar. 24, 1981

[54] METHOD OF VISUALLY DETECTING ANTIOXIDANT IN AN ORGANIC MIXTURE

[75] Inventors: William L. Porter, Cambridge; Roslyn E. Kramer, Boston, both of Mass.

[73] Assignee: The United States of America as represented by the Secretary of the Army, Washington, D.C.

[21] Appl. No.: 114,035

[22] Filed: Jan. 21, 1980

[51] Int. Cl.[3] ...................... G01N 31/06; G01N 31/08
[52] U.S. Cl. .............................. 23/230 M; 23/230 R; 210/656
[58] Field of Search ..................... 23/230 R, 230 M; 210/316

[56] References Cited

PUBLICATIONS

Modern Plastics Encyclopedia, 1968–1969, p. 506.
Chemical Abstracts: 67:34066z; 68:18469y; 83:180720e; 73:91166e; 78:41482n; 80:57596e; 88:69877a.

*Primary Examiner*—Michael S. Marcus
*Attorney, Agent, or Firm*—Nathan Edelberg; Robert P. Gibson; Lawrence E. Labadini

[57] ABSTRACT

Method of screening a mixture of organic compounds to detect the presence of an antioxidant material wherein the organic mixture is first chromatographically separated on a polyamide coated plate and then coated with linoleic acid. The plate is heated until the linoleic acid oxidation products react with the free amine groups on the polyamide material to produce a color change. Antioxidant compounds separated on the plate inhibit the color change and can be visually detected.

4 Claims, No Drawings

METHOD OF VISUALLY DETECTING ANTIOXIDANT IN AN ORGANIC MIXTURE

The invention described herein may be manufactured, used, and licensed by or for the Government for governmental purposes without the payment to us of any royalty thereon.

BACKGROUND OF THE INVENTION

This invention relates to a method of visually detecting the presence of antioxidant activity in organic compounds separated from a mixture of organic compounds separated from a mixture of organic compounds by thin layer chromatography. A rapid qualitative test to determine the presence of an antioxidant in an organic mixture is highly desirable. There are methods which involve the production of fluorescence and the measurement thereof. However, such methods are much more complex than the method of the present invention and they require expensive fluorescence-measuring equipment.

It is, therefore, an object of the present invention to provide a method for visually detecting microquantities of antioxidants separated from organic mixtures by thin layer chromatography.

Other objects will become apparent as the description of the invention proceeds.

SUMMARY OF THE INVENTION

A method of visually detecting an antioxidant in a mixture of organic compounds wherein the organic mixture is separated chromatographically on a polyamide-coated plastic or glass plate forming a plurality of spots on the polyamide coating. Linoleic acid is then spread in a thin layer over the separated spots on the plate and the plate is heated to react oxidation products of linoleic acid with free amine groups in the polyamide coating which reaction produces a brown colored field. If an antioxidant is present in any of the spots, it prevents or reduces the degree of browning reaction, resulting in a creamy-white or yellow spot surrounded by a brown field.

DESCRIPTION OF THE PREFERRED EMBODIMENT

The method of the invention comprises a first step of separating a mixture of organic compounds suspected of containing one or more antioxidants into its component compounds by thin layer chromatography on a polyamide-coated plate. The polyamide-coated plate may be relatively thick and rigid glass plate or a flexible plastic sheet, in either case having a coating of powdered polyamide of at least about 100 microns thickness on the plate. The powdered polyamide is a polymerized epsilon-caprolactam. The mixture of organic compounds is separated in a conventional manner, as is well known in the art for thin layer chromatography separations, into spots of different compounds spaced along the plate.

When the chromatographic separation has been completed, a few microliters of linoleic acid are deposited at the approximate center of each spot on the plate located by long wave ultraviolet light. The linoleic acid spreads to completely cover the spot. The entire plate can alternatively be sprayed with a solution of 10% linoleic acid in petroleum ether.

The polyamide-coated plate containing the linoleic acid deposited on each separated spot is placed on a glass plate of greater area than that of the polyamide-coated plate with the polyamide coating facing upwardly. The assembly of the polyamide-coated plate and the glass plate on which it rests is placed on a shelf in a draft oven and heated for at least 8 hours at about 65° C. to bring about reaction of the linoleic acid oxidation products with the free amine groups in the polyamide coating of the polyamide-coated plate. The polyamide-coated plate is then removed from the draft oven and cooled to ambient temperature. The glass plate eliminates any uneven heating that would occur if the polyamide-coated plate were to rest directly on the shelf of the oven.

The several spots separated on the polyamide-coated plate are observed to determine whether any of them contains creamy-white or yellow areas surrounded by a brown field indicating that an antioxidant is present in that spot. The presence of an antioxidant prevents or slows the reaction between the free amine groups in the polyamide coating and any oxidation products from the linoleic. If no antioxidant is present in the separated spot, the whole area on which linoleic acid is spread forms a solid brown field.

The preferred type of polyamide-coated plate is a flexible, polyethylene terephthalate sheet coated with an approximately 100 micron thick coating of powdered polycaprolactam such as PERLON$_{TM}$ or Polyamide-60. The polyamide is a repeating polypeptide of epsilon-aminocaproic acid with contamination of free primary amino groups. "Polygram", distributed by Brinkmann Instruments, Inc., of Westbury, N.Y., is such a polyamide coated sheet. The polymerized epsilon-caprolactam is a neutral polymer having free amine groups and produces a snow white coating on its substrate.

An alternative polyamide-coated glass plate is distributed by Schleicher and Schuell of Keene, NH as No. G1600/LS 254. It comprises a polymerized epsilon-caprolactam coating of about 120 microns thickness, having a starch binder, and containing an ultraviolet indicator.

The above-described method is applicable to the screening of any mixture of organic compounds to detect the presence of one or more antioxidants therein. It may also be modified for the purpose of isolating such antioxidants. For example, once a determination has been made of the location of a spot on a thin layer chromatogram where an antioxidant is indicated, additional separations may be carried out wherein no linoleic acid is applied, but the identified antioxidant spot or a band across the polyamide-coated plate at the same level may be scraped off of the plate and the antioxidant recovered from the polyamide powder scrapings thus obtained.

The following example illustrates practice of the present invention:

Example 1

Ground, dried clove was placed in a glass extraction column and extracted with petroleum ether. The extract was set aside for future processing. The residue remaining in the column was then extracted with 80 percent ethanol and the ethanol extract was then shaken with ethyl acetate to remove most of the phenolic and polar organic compounds dissolved therein. The ethyl acetate solution was then separated from the 80 percent ethanol solution by means of a separatory funnel. The ethyl acetate solution was evaporated to dryness and the dry residue was taken up in 100 percent ethanol. This solution was then subjected to thin layer chromatographic separation. Five microliters of the solution of material in 100 percent ethanol were deposited about two cm from the bottom edge of a snow-white polyamide-coated plastic plate such as described above. The polyamide-coated plastic plate was set in a developing tank containing a sufficient depth of a mixture of 50% chloroform/50% methanol to wet the bottom edge of the polyamide-coated plastic sheet so that the mixture of 50% chloroform/50% methanol was moved by capillary action upward through the deposit of the material extracted from the ground, dried clove and dissolved in 100 percent ethanol. The mixture of 50% chloroform/50% methanol moving upwardly caused the separation of the material deposited near the bottom edge of the polyamide-coated plate, forming several spots spaced somewhat apart on the polyamide-coated plate. One spot located about 2.5 cm above the deposit of the 100 percent ethanol solution of the material extracted from ground, dried clove was found by the above-described method employing about 20 microliters of linoleic acid to give strong evidence of the presence of an antioxidant in that fraction. Subsequently, it was shown by other methods that this spot was gallic acid. This was partially confirmed by using pure gallic acid in the above-described method of detecting an antioxidant, 5 microliters of the pure gallic acid dissolved in 100% ethanol forming a spot at substantially the same location about 2.5 cm above the deposit of the 100 percent ethanol solution of pure gallic acid on the polyamide-coated plate after subjection to thin layer chromatographic separation as described above, which spot in the test method according to this invention resulted in a creamy-white spot surrounded by a brown field.

It is apparent from the above example that the method of the present invention may be employed in the screening of mixtures of organic compounds for the presence of antioxidants therein. Once the existence of an antioxidant in the mixture of organic compounds has been established, identification of the antioxidant may be accomplished by other procedures after enough of the antioxidant has been isolated to permit analysis thereof. The above described screening or detecting method for antioxidants has been used with thyme and other naturally occurring materials which contain antioxidants. The method will doubtless hasten the time when most naturally occurring mixtures of organic compounds will have been screened for the presence of antioxidants therein and it will become easier to proceed to the identification and characterization of the antioxidants in such naturally occurring mixtures.

In cases where there are volatile antioxidants in organic compound mixtures, the method may include covering the separated spots on the polyamide-coated plate with a glass plate or a sheet of plastic after linoleic acid has been deposited and before heating in the draft oven occurs. The plastic sheet must, of course, inhibit sublimation of the antioxidant for the method to be successful in detecting volatile antioxidants.

We claim:

1. A method of visually detecting the antioxidant gallic acid in a mixture of organic compounds which comprises the steps of:
   a. separating a mixture of organic compounds into its component compounds by thin layer chromatography by contacting a mixture of organic compounds suspected of containing the antioxidant gallic acid with a polyamide-coated plate, said polyamide-coated plate comprising a sheet or plastic or glass supporting a coating of powdered polyamide of about 100 to about 120 microns thickness, said polyamide being polymerized epsilon-caprolactam, said mixture of organic compounds being separated on said polyamide-coated plate into at least two spaced-apart spots, each of said spots being the site of a different compound from the others of said spots;
   b. depositing a thin layer of linoleic acid over each of said spaced-apart spots;
   c. placing said polyamide-coated plate, containing said linoleic acid deposited thereon, in an oven at about 65° C. and heating said polyamide-coated plate for at least 8 hours at about 65° C.;
   d. removing said polyamide-coated plate from said oven; and
   e. observing said spots and the adjacent areas of said polyamide-coated plate for color differences in reflected light, the presence of a creamy-white or yellow color where one of said spaced-apart spots was located surrounded by a brown field indicating the presence of an antioxidant in the creamy-white or yellow spot, a solid brown field lacking any creamy-white or yellow color indicating the absence of antioxidant from said one of said spaced apart spots.

2. A method according to claim 1, wherein in step (c) said polyamide-coated plate is covered with a glass or plastic plate prior to the heating of said polyamide-coated plate in said oven to prevent the escape of volatile antioxidant from said spot on said polyamide-coated plate, whereby said spot remains creamy-white or yellow surrounded by a brown field.

3. A method according to claim 1 wherein in step (c) said polyamide-coated plate is placed on a glass plate of greater area than said polyamide-coated plate with said coating of powdered polyamide facing upwardly and not in contact with said glass plate and then heating said polyamide-coated plate supported on said glass plate.

4. A method according to claim 1 wherein in step (b) about 20 microliters of linoleic acid is deposited at the center of each spaced-apart spot, said linoleic acid spreading to cover the spot.

* * * * *